US010502723B2

(12) United States Patent
Cai et al.

(10) Patent No.: US 10,502,723 B2
(45) Date of Patent: Dec. 10, 2019

(54) BREATH SENSOR APPARATUS (71) Applicant: NITTO DENKO CORPORATION, Osaka (JP)

(72) Inventors: Jie Cai, Oceanside, CA (US); Qianxi Lai, Carlsbad, CA (US); Ekambaram Sambandan, Carlsbad, CA (US); Evan Miller, Springfield, OR (US)

(73) Assignee: Nitto Denko Corporation, Osaka (JP)

( * ) Notice: Subject to any disclaimer, the term of this patent is extended or adjusted under 35 U.S.C. 154(b) by 81 days.

(21) Appl. No.: 15/519,355

(22) PCT Filed: Oct. 16, 2015

(86) PCT No.: PCT/US2015/056012
§ 371 (c)(1),
(2) Date: Apr. 14, 2017

(87) PCT Pub. No.: WO2016/061501
PCT Pub. Date: Apr. 21, 2016

(65) Prior Publication Data
US 2017/0227508 A1 Aug. 10, 2017

Related U.S. Application Data

(60) Provisional application No. 62/064,680, filed on Oct. 16, 2014.

(51) Int. Cl.
*G01N 33/00* (2006.01)
*A61B 5/087* (2006.01)
(Continued)

(52) U.S. Cl.
CPC ......... *G01N 33/0016* (2013.01); *A61B 5/082* (2013.01); *A61B 5/0803* (2013.01);
(Continued)

(58) Field of Classification Search
CPC ............ G01N 33/497; G01N 33/4972; G01N 2033/4975
See application file for complete search history.

(56) References Cited

U.S. PATENT DOCUMENTS 3,877,291 A 4/1975 Hoppesch et al.
4,161,875 A 7/1979 Cornelis et al.
(Continued)

FOREIGN PATENT DOCUMENTS

CN 103344775 A 10/2013
EP 0327396 A2 * 8/1989 ......... G01N 33/4972
(Continued)

OTHER PUBLICATIONS

Wang, L. et al., "Nanosensor Device for Breath Acetone Detection", Sensor Letters, vol. 8, No. 5, Oct. 1, 2010, pp. 709-712.*
(Continued)

*Primary Examiner* — Daniel S Larkin
*Assistant Examiner* — Anthony W Megna Fuentes
(74) *Attorney, Agent, or Firm* — K&L Gates LLP; Louis C. Cullman; Hal Gibson (57) ABSTRACT

A breath sensor apparatus for detecting the presence of a compound in an exhaled gas sample, the apparatus comprising a chamber for retaining a gas sample, the chamber defining a gas inlet and a gas outlet, a sensor inside the chamber for analyzing the gas sample, an airflow disrupting element disposed proximate to the sensor to affect the airflow near the device, and an airflow reducing element disposed over the gas outlet to increase the retention time of the gas sample within the chamber.

11 Claims, 5 Drawing Sheets

(51) Int. Cl.
*G01N 33/497* (2006.01)
*A61B 5/08* (2006.01)
*A61B 5/097* (2006.01)

(52) U.S. Cl.
CPC .............. *A61B 5/087* (2013.01); *A61B 5/097* (2013.01); *G01N 33/0047* (2013.01); *G01N 33/497* (2013.01); *G01N 33/0036* (2013.01); *G01N 2033/4975* (2013.01)

(56) References Cited

U.S. PATENT DOCUMENTS

| | | | | |
|---|---|---|---|---|
| 5,454,375 | A * | 10/1995 | Rothenberg | A61B 5/087 600/533 |
| 5,759,368 | A * | 6/1998 | Kuhn | G01N 27/4045 204/403.01 |
| 5,787,885 | A | 8/1998 | Lemelson | |
| 6,467,333 | B2 * | 10/2002 | Lewis | A61B 5/00 422/84 |
| 6,656,127 | B1 * | 12/2003 | Ben-Oren | A61B 5/083 600/529 |
| 7,220,387 | B2 * | 5/2007 | Flaherty | A61B 5/097 356/433 |
| 8,756,974 | B2 | 6/2014 | Mitchell | |
| 8,783,089 | B2 * | 7/2014 | Cartier | G01N 1/2208 73/23.3 |
| 8,950,240 | B2 * | 2/2015 | Yeh | G01N 33/0047 257/252 |
| 2003/0121309 | A1 * | 7/2003 | Fikus | G01N 27/4045 73/23.3 |
| 2009/0054479 | A1 | 2/2009 | Conner et al. | |
| 2011/0239735 | A1 * | 10/2011 | Setayesh | G01N 33/0037 73/23.3 |
| 2013/0091924 | A1 * | 4/2013 | Scheffler | G01N 33/007 73/23.3 |
| 2013/0115706 | A1 | 5/2013 | Gouma | |
| 2013/0125618 | A1 * | 5/2013 | Hiranaka | G01N 21/783 73/23.3 |
| 2013/0193004 | A1 * | 8/2013 | Scheffler | G01N 27/304 205/785.5 |
| 2014/0275857 | A1 | 9/2014 | Toth et al. | |
| 2014/0366610 | A1 * | 12/2014 | Rodriguez | G01N 33/497 73/23.3 |
| 2015/0346190 | A1 | 12/2015 | Sambandan | |

FOREIGN PATENT DOCUMENTS

| | | |
|---|---|---|
| EP | 0327396 A3 | 10/1990 |
| JP | 2002031615 | 1/2003 |
| WO | 2010/094967 | 8/2010 |
| WO | 2014/031072 | 2/2014 |

OTHER PUBLICATIONS

Righettoni et al., Portable gas sensor for breath analysis, Nanotech Conference & Expo 2011: An Interdisciplinary Integrative Forum on Nanotechnology, Biotechnology and Microtechnology, Boston, MA, United States, Jun. 13-16, 2011 (2011), 3, 9-11.

Righetonni, M. et al., "Thermally Stable, Silica-Doped [epsilon]-WO 3 for Sensing of Acetone in the Human Breath", Chemistry of Materials, vol. 22, No. 10, May 25, 2010, pp. 3152-3157.

Richetonni, M. et al., "Breath Acetone Monitoring by Portable Si:WOgas Sensors", Analytica Chimica Acta, Elsevier, Amsterdam, NL, vol. 738, Jun. 3, 2012, pp. 69-75.

Wang et al., Chem Mater., 20:4794-4796 (2008).

Choi et al., Selective Diagnosis of Diabetes Using Pt-Functionalized WO3 Hemitube Networks As a Sensing Layer of Acetone in Exhaled Breath, Analytical Chemistry (Washington, DC, United States) (2013), 85(3), 1792-1796.

* cited by examiner

BREATH SENSOR APPARATUS

CROSS REFERENCE TO RELATED APPLICATIONS

This application is a national phase of PCT/US2015/056012 filed on Oct. 15, 2015, which claims priority to U.S. 62/064,680 filed on Oct. 16, 2014, the entire disclosures of which are incorporated herein by reference.

FIELD

The invention relates to an apparatus for delivering a gas sample to a volatile organic compound (VOC) sensor. More particularly, the present invention relates to an apparatus for receiving a sample of exhaled breath from an individual and delivering the sample of the breath to a solid state VOC sensor.

BACKGROUND

Various sensors have been used to detect the presence of compounds in a gas sample, e.g., U.S. Patent Publication Nos. 2009/0054799 and 2013/0115706, U.S. Pat. No. 5,787,885, Figaro TGS 822 Sensor (http://www.figarosensor.com/products/822pdf.pdf), Breath acetone monitoring by portable Si:$WO_3$ gas sensors" (Analytica Chimica Acta 738 (2012) 69-75). However, some acetone sensing devices require higher than ambient operating temperatures. In some cases, the sensors operate at very high temperatures, between 100° C. and 500° C., see Wang, et al., Chem. Mater., 20:4794-4796 (2008); Wang et al., Sensor Letters, 8:1-4 (2010); Righettoni et al., Anal. Chem., 82:3581-3587 (2010). For environmental gas sensors, a heated sensor chip is placed in a mesh enclosed chamber within the device. In order to protect the temperature field around the heated sensor chip and to maintain the temperature of the sensor, the analyte is only allowed to reach the sensor by diffusion. However, when analyzing compounds from breath, the analyte comes in contact with the sensor by a flow mechanism (i.e., an exhaled breath or mechanical discharge), which alters the pre-established equilibrium around the heated sensor. As a result of their small size and the temperature difference between the sensor and exhaled breath, flow over the sensor causes heat loss by convection. Exhaled breath also has high moisture content, which can cool down the sensor.

When a gas sample at body temperature directly contacts the sensor surface, the sensor surface cools down quickly by convection which can result in inaccurate measurements. Moreover, the flow rate of human-exhaled breath varies from person to person so that the convection heat loss cannot be easily predicted. The heat loss can cause the temperature of the sensor to drop below the sensor's operating temperature, requiring the sensor to heat up again to operate. These temperature fluctuations can result in inconsistent and/or inaccurate results.

Therefore, there remains a need in the art for a breath sensor apparatus that reduces temperature fluctuation caused by flow rates in order to obtain more consistent and accurate results. The disclosed apparatus provides more consistent and accurate results for detecting volatile organic compounds from exhaled breath by reducing the flow rate variation through flow redistribution using a fixed element.

SUMMARY

A breath testing apparatus is described comprising a chamber for retaining a gas sample, a gas inlet, a gas outlet, a solid state sensor device, and an airflow disrupting element positioned near the sensor to redistribute the flow of the gas sample, so that the flow rate on the sensor surface changes less even if there are variations in initial flow rate and the sensor maintains the necessary operating temperature to yield consistent results.

Some embodiments include a breath testing apparatus comprising a chamber for retaining a gas sample, a gas inlet in fluid communication with the chamber, and a gas outlet in fluid communication with the chamber; a sensor disposed within the chamber, and in fluid communication with the gas inlet and the gas outlet; and an airflow disrupting element disposed within the chamber and sufficiently close to the sensor to change the velocity of air flowing over a surface of the sensor, wherein the airflow disrupting element occupies 95% or less of the cross-sectional area of the chamber and is in fluid communication with the gas inlet, the gas outlet, and the sensor.

The disclosed apparatus provides more consistent results by reducing the heat lost to convection. This breath test chamber is useful for detecting volatile organic compounds in the breath.

These and other embodiments are described in greater detail below.

DETAILED DESCRIPTION

Typically, a breath testing apparatus can comprise a chamber for retaining a gas sample, a gas inlet in fluid communication with the chamber, and a gas outlet in fluid communication with the chamber. Thus, gas that flows into the gas inlet, e.g. by exhaled breath, can flow into the chamber from the gas inlet, and out of the chamber through the gas outlet. Within the chamber is a sensor that is also in fluid communication with the gas inlet and the gas outlet, such that gas flowing through the device through the gas inlet will come into contact with the sensor. The chamber also contains an airflow disrupting element that sufficiently close to the sensor to change the velocity of air flowing over a surface of the sensor. The airflow disrupting element should occupies 95% or less of the cross-sectional area of the chamber and be in fluid communication with the gas inlet, the gas outlet, and the sensor.

Gas Inlet

A gas inlet may be any structural feature that allows gas to flow into the chamber, such as an aperture or hole, a tube, etc. Some gas inlets may be in the form of a mouthpiece, such as a mouthpiece arranged to deliver an expiratory breath to the chamber. It may also be helpful for gas inlet to comprise, or be coupled to, a valve to contain an expiratory breath in the chamber and prevent any portion of the breath from escaping out the gas inlet.

A gas inlet may have any suitable diameter, such as a diameter in a range of about 1 mm to about 5 cm, about 2 mm to about 2 cm, about 5 mm to about 1.5 cm, about 1 cm, or any other diameter in a range bounded by any of these values.

Chamber

A chamber may be any structural feature that is suitable for retaining a gas sample. For example, a chamber may be a container of any of a variety of three-dimensional geometric shapes such as, but not limited to, a cylinder, an elliptical cylinder, a rectangular cylinder, a geometrical cylinder having a base of any shape, or any shape suitable for retaining a gas sample.

For breath analysis, the chamber may be intended to hold a gas sample such as an exhaled animal breath, or a portion thereof. In some embodiments, the volume of the chamber may be equal to or less than the lung capacity of an animal such as a human being. In some embodiments, the chamber's volume may be about 0.5 mL, about 1 mL, about 5 mL, about 6 mL, about 7 mL, about 8 mL, about 9 mL, about 10 mL, about 20 mL, about 30 mL, about 40 mL, about 50 mL, about 60 mL, about 70 mL, about 80 mL, about 90 mL, about 100 mL, about 200 mL, about 500 mL, about 1,000 mL, or any other volume in a range bounded by any of these values.

In some embodiments, the chamber is a right circular cylinder with a diameter of 2.6 cm The chamber may be composed of any suitable material. It may be helpful for the chamber to be formed from a material that does not melt or burn, evolve compounds or gases that affect the sensor's measurement, or corrode under normal operating conditions for a breath testing apparatus.

Sensor

The sensor may be any component which changes or otherwise indicates the presence of any analyte.

In some embodiments, a sensor may be a catalytic material, such as a metal oxide catalyst. There are a number of principles which may be used to detect an analyte. For example, an analyte may be detected by a change in an electrical property, such as resistivity. A change in an electrical property might be detected, for example, by connecting the catalytic material to an electrode. When the catalytic material catalyzes a reaction of the analyte, the electrical property, such as resistivity or resistance, could be affected. This could be detected via electrical contact between the electrode and the catalyst.

Some useful catalysts include tungsten oxides, such as $WO_3$, including ε-phase $WO_3$. Some tungsten oxide catalysts may be doped with boron and/or loaded with platinum.

In some embodiments, the sensor comprises, or is, a tungsten oxide catalysts doped with boron. In some embodiments, the sensor comprises, or is, a tungsten oxide catalyst loaded with platinum.

In some embodiments, the sensor comprises, or is, $WO_3$, such as ε-phase $WO_3$.

In some embodiments, the sensor comprises, or is, $WO_3$, such as ε-phase $WO_3$, and is doped with boron.

In some embodiments, the sensor comprises, or is, $WO_3$, such as ε-phase $WO_3$, and is loaded with platinum.

In some embodiments, the sensor comprises, or is, a tungsten oxide, such as $WO_3$, or ε-phase $WO_3$, which is doped with boron and is loaded with platinum.

For catalysts that are boron doped, meaning doped with boron atoms or ions of boron, any suitable amount of boron dopant may be used, such as about 0.1 atom % to about 20 atom %, about 0.5 atom % to about 10 atom %, about 4 atom % to about 10 atom %, about 6 atom %, or any other amount in a range bounded by any of these values.

For catalysts that are loaded with platinum, meaning platinum atoms or ions of platinum, any suitable amount of platinum metal or ion may be used, such as about 0.1% to about 10%, about 0.2% to about 4%, about 0.5% to about 2%, about 1%, or any other amount in a range bounded by any of these values based upon the weight of the catalyst including the platinum.

The sensor may be useful for detecting any analyte of interest, such as volatile organic compounds including, but not limited to, $SO_N$, $NO_R$, etc. In some embodiments, the sensor may be useful for detecting acetone.

Airflow Disrupting Element

An airflow disrupting element may be any structural component which, when appropriately positioned, changes the turbulence of air flowing over the surface of the sensor. An airflow disrupting element may be any structural component which, when appropriately positioned, changes the velocity of air flowing over the surface of the sensor. Typically, the airflow disrupting element may be positioned so that air entering through the gas inlet is affected by the airflow disrupting element before the entering air comes in contact with the sensor. Typically, the airflow disrupting element may be positioned so that air flow passing over the sensor is increased before the entering air comes in contact with the sensor. Typically, the airflow disrupting element may be positioned so that air flow passing over the sensor is made more turbulent before the entering air comes in contact with the sensor.

Figure 1A:
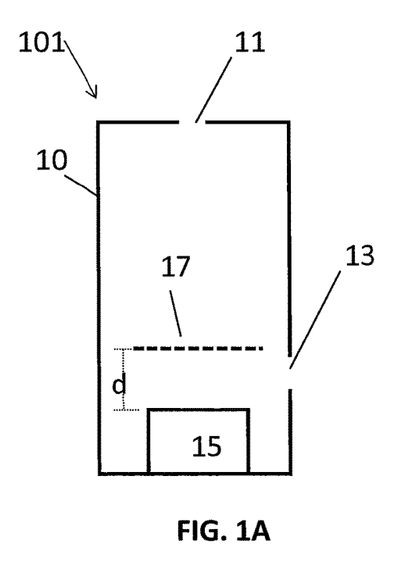
FIG. 1A is a schematic of an embodiment of the breath sensor apparatus.

The rate of heat loss by convection can be affected by the distance d between the airflow disrupting element and the sensor. See FIGS. 1A and 1B. In some embodiments, the airflow disrupting element may be disposed proximate to the sensor, such that the airflow disrupting element is sufficiently close to the sensor to change the velocity of the airflow over the surface of the sensor. In some embodiments, the airflow disrupting element may be disposed proximate to the sensor, such that the airflow disrupting element is sufficiently close to the sensor to change the turbulence of the airflow over the surface of the sensor. While not wanting to be bound by any theory, it is believed that an airflow disrupting element that is too close to the sensor may reduce airflow to only diffuse airflows across the sensor, resulting in inaccurate sensor readings, and that an airflow disrupting element that is too far from the sensor may not sufficiently affect the airflow velocity over the sensor surface. In some embodiments, the distance d between may be about 1 mm, about 2 mm, about 3 mm, about 4 mm, about 5 mm, about 6 mm, about 7 mm, about 8 mm, about 9 mm, about 10 mm, about 20 mm, about 30 mm, about 40 mm, about 50 mm, about 100 mm, about 200 mm, or any other distance in a range bounded by any of these values.

In some embodiments, the airflow disrupting element comprises a mesh screen. The open area of a mesh screen, including the portion of the surface area of the element that a gas sample can flow through, e.g., the space between the metal strands of a mesh screen, may be any suitable value, such as between about 5% and about 95%, about 10% to about 70%, about 10% to about 80%, about 15% to about 50%, about 20% to about 40%, about 30% to about 50%, about 30% to about 40%, or any percentage in a range bounded by any of these values.

In some embodiments, the airflow disrupting element may comprise a plurality of mesh screens, a solid plate, a plurality of solid plates, a baffle, a plurality of baffles, a perforated sheet or disk, a slat, a plurality of slats, or a plurality of elements to affect the airflow inside the chamber.

In some embodiments, the airflow disrupting element may substantially fill the cross-sectional area of the chamber. For example, the airflow disrupting element may fill about 5%, about 6%, about 7%, about 8%, about 9%, about 10%, about 15%, about 20%, about 25%, about 35%, about 40%, about 50%, about 55%, about 60%, about 65%, about 70%, about 75%, about 80%, about 90%, about 100%, or any other percentage any a range bound by any of these values, of the cross-sectional area of the chamber. In some embodiments, the airflow disrupting element may be at least the cross-sectional surface parameters of the sensor surface. An airflow disrupting element is said to fill the portion of the cross-sectional area of the chamber as determined by the outer boundary of the element, e.g. a screen with a 1 cm radius in a chamber with a 2 cm radius is said to fill 25% of the cross sectional area of the chamber regardless of the open area of the screen. In some embodiments, an annular spacing may be defined between the chamber side wall and the airflow disrupting element. In some embodiments, the annular spacing provides increased air flow over the surface of the sensor. In some embodiments, the annular spacing provides increased air flow turbulence over the surface of the sensor. In some embodiments the annular space may be at least the inside diameter of the chamber minus the surface length/width parameters of the sensor surface.

The airflow disrupting element may be composed of any suitable material. It may be helpful for the airflow disrupting element to be formed from a material that does not melt or burn, evolve compounds or gases that affect the sensor's measurement, or corrode under normal operating conditions for the breath testing apparatus. In some embodiments, the airflow disrupting element may comprise a metal, such as, but not limited to, aluminum, stainless steel, tin, nickel, copper, titanium, cobalt, zinc, silver, gold, tungsten, platinum, lead, or any combination thereof. In other embodiments, the airflow disrupting element may comprise a non-metal material, such as, but not limited to, a ceramic, porous ceramic, glass wool, polymer, combinations thereof, or any other appropriate material.

For some devices, the airflow disrupting element may provide plural airflow impinging upon and/or adjacent to the sensor element. For example, the airflow element may provide a first airflow impinging upon the sensor surface at a first velocity and a second airflow impinging upon the sensor surface at a second velocity. In some embodiments, the airflow originating through the space defined between the inside surface of the chamber and the edge of the airflow disrupting element, may result in a first airflow, for example, a higher velocity. In some embodiments, the first airflow velocity may greater than the second airflow velocity. In some embodiments, the airflow originating through the airflow disrupting element may result in a second airflow velocity. In some embodiments, the second airflow velocity is greater than the first airflow velocity. In some embodiments, a mixing area above the sensor element surface and below the lower surface of the airflow disrupting element, provides an area for the mixing of the plural velocity airflows, thereby contributing to the reduction of the convective heat loss at the sensor surface.

For some devices, the airflow disrupting element may provide plural airflow impinging upon and/or adjacent to the sensor element. For some devices, the airflow disrupting element may provide turbulent airflow impinging upon and/or adjacent to the sensor element. For example, the airflow element may provide a first airflow impinging upon the sensor surface at a first angle and a second airflow impinging upon the sensor surface at a second angle. In some embodiments, a mixing area above the sensor element surface and below the lower surface of the airflow disrupting element, provides an area for the mixing of the plural angular airflows, thereby contributing to the reduction of the convective heat loss at the sensor surface.

In some embodiments, the airflow disrupting element may change the airflow across the surface of the sensor to a turbulent airflow. The term "turbulent," as used herein, refers to airflow that may be wavy, cyclonic, chaotic, form eddies, or other airflow patterns that are not parallel to the plane of the sensor device's surface. Without wanting to be bound by any theory, it is believed that an airflow parallel to and across the surface of the sensor can reduce the temperature of the sensor at a greater rate, and by changing the airflow near the sensor to turbulent flow, the sensor will maintain an operating temperature with less energy required to heat the sensor.

In some embodiments, the airflow disrupting element may alter the airflow such that the velocity of the airflow past the sensor and parallel to the sensor's surface is substantially reduced. While not wanting to be bound by any theory, it is believed that by altering the airflow in this manner, the airflow disrupting element can reduce the rate at which the sensor loses heat by convection. In some embodiments, the airflow past the surface of the sensor may be about 50 mL/min, about 100 mL/min, about 110 mL/min, about 120 mL/min, about 130 mL/min, about 140 mL/min, about 150 mL/min, about 200 mL/min, about 300 mL/min, about 400 mL/min, about 500 mL/min, about 1,000 mL/min, about 1,500 mL/min, about 2,000 mL/min, about 3,000 mL/min, about 4,000 mL/min, about 5,000 mL/min, about 10,000 mL/min, about 20,000 mL/min, about 30,000 mL/min, about 50,000 mL/min or any other airflow rate in a range bounded by any of these values.

In some embodiments, an airflow disrupting element is a stainless steel wire mesh disk, with a wire diameter of 0.0045 in, a mesh size of 100×100, an opening size of 0.0055 in, creating an open area of about 36%; a diameter of 1.5 cm, and is positioned 1.0 cm vertically above a sensor.

Gas Outlet

A gas outlet includes any structural feature, such as an aperture or hole, a tube, etc., which can allow gas to flow from the chamber when pressure is applied to the gas inlet.

A gas outlet may be positioned in any position that allows fluid communication between the gas outlet and the chamber. In some embodiments, the gas outlet may be disposed in the side wall, in the top, or bottom of the chamber. In some embodiments, the gas outlet may be an aperture or hole of between about 0.1 cm$^2$ to about 10 cm$^2$, about 1 cm$^2$ to about 5 cm$^2$, about 1.5 cm$^2$ to about 4.5 cm$^2$, about 2 cm$^2$ to 4 cm$^2$, about 2.5 cm$^2$ to about 3.5 cm$^2$, about 3 cm$^2$ or any other distance in a range bounded by any of these values.

Airflow Reducing Element

A gas outlet can further comprise an airflow reducing element. An airflow reducing element could be any structural feature that can reduce the velocity or flow rate of air flowing out of the gas outlet. The airflow reducing element may help retain the gas sample in the chamber and allow sufficient time for the sensor to accurately determine the amount of a target analyte contained in the gas sample.

The airflow reducing element may be composed of any suitable material. It may be helpful for the airflow reducing element to be formed from a material that does not melt or burn, evolve compounds or gases that affect the sensor's measurement, or corrode under normal operating conditions for the breath testing apparatus. In some embodiments, the airflow reducing element may comprise a metal, such as, but not limited to aluminum, stainless steel, tin, nickel, copper, titanium, iron, cobalt, zinc, silver, gold, tungsten, platinum, lead, or combinations thereof. In other embodiments, the airflow reducing element may comprise a non-metal component. The airflow reducing element may include, but is not limited to, ceramic, porous ceramic, glass, wool, polymer, combinations there of, or any other appropriate material.

In some embodiments, the airflow reducing element may comprise a mesh screen, such as a metal mesh screen. In some embodiments, the mesh screen have an open area of about 5%, about 6%, about 7%, about 8%, about 9%, about 10%, about 15%, about 20%, about 25%, about 50%, about 60%, about 70%, about 80%, about 90%, about 99%, or any other percentage in a range bounded by any of these values. In some embodiments, the airflow reducing element may have an open area between about 15% and 50% or an open area of about 36%.

In some embodiments, a gas outlet has a 1.0 cm diameter, is located in the wall of the chamber about 5 cm above the second end of the apparatus, and has an airflow reducing element that is a stainless steel wire mesh screen having 30% opening which completely covers the area of the gas outlet. FIGS. 1A, 1B, 7, and 8 depict a schematic of an embodiment of the breath sensor apparatus. The apparatus 101 comprises a chamber 10 for retaining a gas sample, a sensor 15 for analyzing the gas sample, and an airflow disrupting element 17 for affecting the airflow near the sensor 15. The annular space (not numbered) is defined between the chamber 10 and the airflow disrupting element 17. The apparatus may also comprise a gas inlet 11 for introducing a gas sample into the chamber. In some embodiments, the gas inlet 11, airflow disrupting element 17, and sensor 15, may be arranged co-axially so as to substantially reduce the amount of gas sample that travels from the gas inlet 11 to the sensor 15 un-impinged.

In some embodiments, the plane of the sensor 15 and/or the airflow disrupting element 17 may be oblique relative the general airflow passing from the gas inlet 11. In some embodiments, the plane of the sensor 15 and/or the airflow disrupting element 17 may be substantially perpendicular, e.g., about 75° to about 90° relative the general airflow passing from the gas inlet 11. In some embodiments, the general direction of the airflow passing from the gas inlet may be substantially coaxial with the axis of the gas inlet 11 and/or the chamber 10. The gas inlet may be disposed above and/or enclosing the airflow disrupting element 17 and/or the sensor 15. The sensor 15 may be a solid state sensor for detecting the presence of volatile organic compounds (VOCs) in the gas sample, such as acetone. In some embodiments, the apparatus 101 may comprise a gas outlet 13. In some embodiments, the gas outlet 13 may be disposed such that the gas sample flowing from the gas inlet 11 to the sensor 15 may or may not need to change direction before flowing out of the gas outlet 13.

In some embodiments, the gas inlet 11, airflow disrupting element 17, and sensor 15 may be co-axial, and the gas outlet 13 may be disposed in the wall of the chamber 10, oriented obliquely (between about 0° and about 90°) or perpendicular (90°) to the axis of the aforementioned components. In some embodiments, the annular space may provide fluid communication between the airflow disrupting element 17 and the chamber 10. In some embodiments, the annular space may provide fluid communication between the airflow disrupting element 17 and the sensor 15. The gas inlet 11 may be in fluid communication with the sensor 15, the airflow disrupting element 17, and the gas outlet 13. The gas outlet 13 may be in fluid communication with the gas inlet 11, the sensor 15, and the airflow disrupting element 19.

Figure 1B:
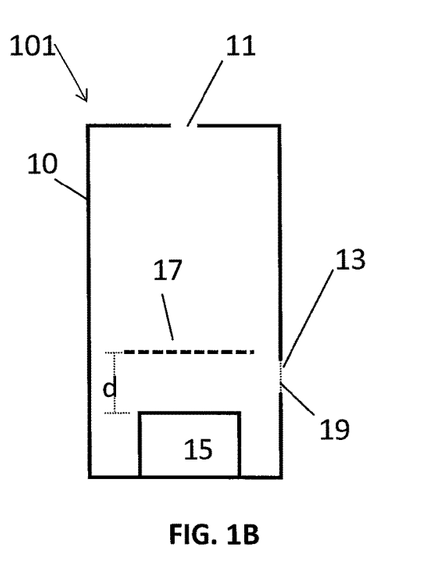
FIG. 1B is a schematic of an embodiment of the breath sensor apparatus with an additional airflow reducing element.

While not intending to be bound by any theory, it is believed that multiple factors may contribute to the effectiveness and the consistency of results produced by the sensor 15. These factors may include, but are not limited to, the open area of the airflow disrupting element, the portion of the cross-section of the chamber filled by the airflow disrupting element, the distance d between the airflow disrupting element 17 and the sensor 15, and the open area of an airflow reducing element 19, as shown in FIG. 1B.

Figure 2A:
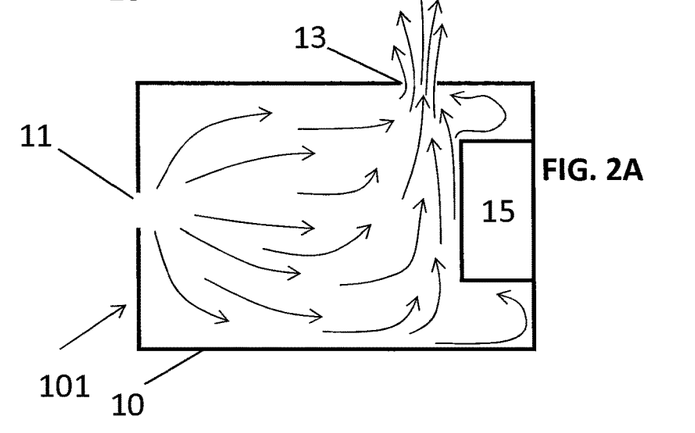
FIG. 2A is a schematic of the airflow through the breath sensor apparatus without an airflow disrupting element or airflow reducing element.
Figure 2B:
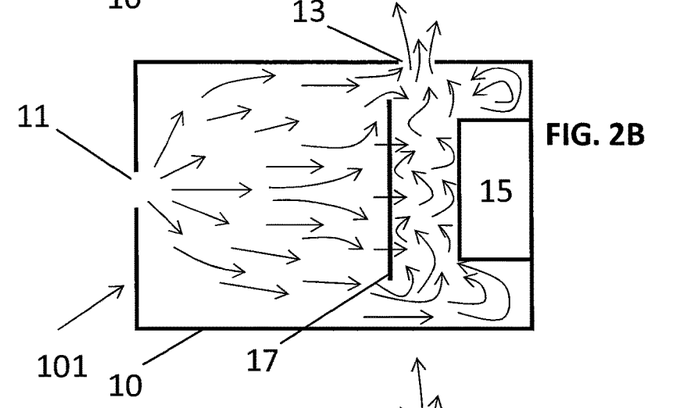
FIG. 2B is a schematic of the airflow through the breath sensor apparatus with an airflow disrupting element.
Figure 2C:
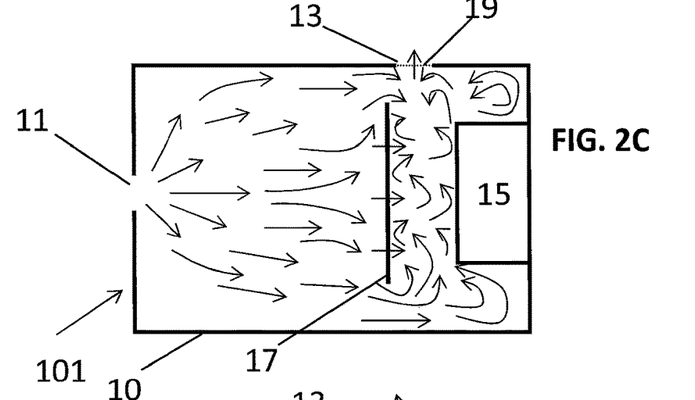
FIG. 2C is a schematic of the airflow through the breath sensor apparatus with an airflow disrupting element and an airflow reducing element.

As demonstrated in FIGS. 2A-2C, the air flow is predicted to behave differently based on the selected components of the apparatus. FIG. 2A shows the apparatus 101 with the airflow entering through the gas inlet 11 of the chamber 10 and towards the sensor 15. The airflow may then exit through the gas outlet 13 generally unobstructed and without necessarily allowing the sensor 15 enough time to provide an accurate reading of the target analyte. FIG. 2B shows how the airflow pattern may change with the inclusion of an airflow disrupting element 17 into the chamber. Without wanting to be bound by any theory, it is believed that the airflow disrupting element 17 causes the airflow to remain in the chamber 10 for a longer time and allow the sensor 15 more time to test for the target analyte. FIG. 2C shows how the airflow pattern may change with the inclusion of both an airflow disrupting element 17 and an airflow reducing element 19. Without wanting to be bound by any theory, it is believed that the inclusion of both an airflow disrupting element 17 and an airflow reducing element 19 will cause the airflow remain within the chamber 10 longer than either component alone and providing the sensor 15 more time to test for the target analyte.

Figure 10:
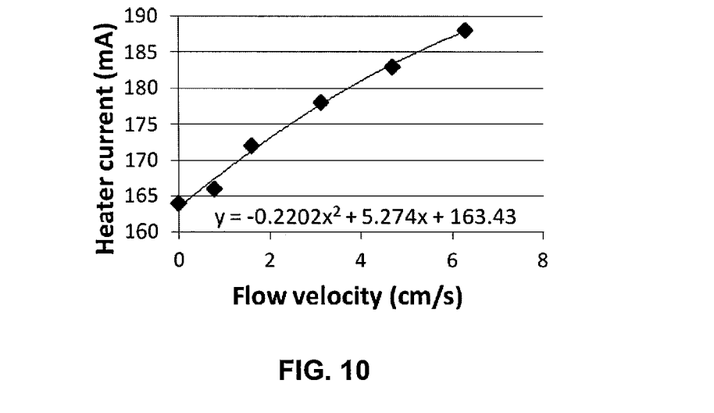
FIG. 10 is a graph depicting the relationship between flow rate and current through a heater element.

In some embodiments, the airflow disrupting element may reduce the convective heat loss by about 1%, about 2%, about 3%, about 4%, about 5%, about 10%, about 20%, about 25%, about 50%, about 60%, about 70%, about 75%, about 80%, about 90%, about 100% or any other percentages in a range bounded by any of these values. The amount of conductive heat loss can be measured by the change in the current through the heater circuit, as shown in FIG. 10. Maintaining the operating temperature of the sensor can result in more consistent results.

In another embodiment, the chamber may be a right circular cylinder with a diameter of 2.6 cm, a gas inlet having a 1.0 cm diameter located in the first end of the apparatus; an airflow disrupting element that is a stainless steel wire mesh disk, with a wire diameter of 0.0045 in, a mesh size of 100×100, an opening size of 0.0055 in, creating an open area of about 36%; a diameter of 1.5 cm, and is positioned 1.0 cm vertically above a sensor, a gas outlet having a 1.0 cm diameter located in the wall of the chamber about 5 cm above the second end of the apparatus, and an airflow reducing element that is a stainless steel wire mesh screen having 30% opening which completely covers the area of the gas outlet.

The following embodiments are specifically contemplated:

Embodiment 1

A breath testing apparatus comprising:
a chamber for retaining a gas sample, a gas inlet in fluid communication with the chamber, and a gas outlet in fluid communication with the chamber;
a sensor disposed within the chamber, and in fluid communication with the gas inlet and the gas outlet; and
an airflow disrupting element disposed within the chamber and sufficiently close to the sensor to change the velocity of air flowing over a surface of the sensor, wherein the airflow disrupting element occupies 95% or less of the cross-sectional area of the chamber and is in fluid communication with the gas inlet, the gas outlet, and the sensor.

Embodiment 2

The apparatus of embodiment 1, wherein the sensor comprises boron-doped tungsten oxide.

Embodiment 3

The apparatus of embodiment 2, wherein the tungsten oxide is ε-phase WO3.

Embodiment 4

The apparatus of embodiment 2 or 3, wherein the boron-doped tungsten oxide is loaded with platinum.

Embodiment 5

The apparatus of embodiment 1, 2, 3, or 4, wherein the sensor is sensitive to the presence of a volatile organic compound.

Embodiment 6

The apparatus of embodiment 1, 2, 3, 4, or 5, further comprising an electrode in electrical communication with the sensor, and the apparatus is configured to detect a volatile organic compound by a change in resistance of the sensor.

Embodiment 7

The apparatus of embodiment 5 or 6, wherein the volatile organic compound is acetone.

Embodiment 8

An apparatus of embodiment 1, 2, 3, 4, 5, 6, or 7, wherein the airflow disrupting element comprises a mesh screen.

Embodiment 9

The apparatus of embodiment 8, wherein the open area of the mesh screen is between about 5% and about 95%.

Embodiment 10

The apparatus of embodiment 1, 2, 3, 4, 5, 6, 7, 8, or 9, wherein the further comprising an airflow reducing element coupled to a gas outlet.

Embodiment 11

The apparatus of embodiment 10, wherein the airflow reducing element comprises a mesh screen.

Embodiment 12

The apparatus of embodiment 11, wherein the open area of the airflow reducing element mesh screen is between about 15% and about 50%.

EXAMPLES

Example 1

Figure 3:
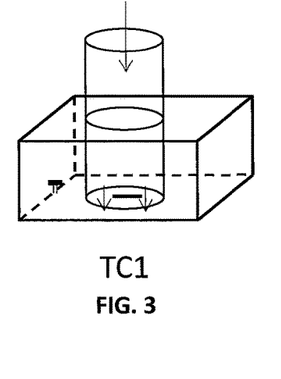
FIG. 3 a schematic of the test chamber TC1 as described in Example 1.

A test chamber 1 (TC1) was built, a schematic of TC1 is shown in FIG. 3, including a 1% Pt-ε-WO$_3$ acetone sensor as described in U.S. Provisional Patent Application No. 62/003,753 and as follows.

Making Boron-Doped ε-Phase WO$_3$

Ammonium meta tungstate hydrate (5 g), boric acid (100 mg), carbohydrazide [fuel] (2 g), and ammonium nitrate [oxidizier] (10 g) were dissolved in 50 mL of deionized (DI) water. The aqueous solution was then placed in a muffle furnace, which had been preheated to about 420° C. The aqueous solution was heated for about 20 min or until combustion of the materials was substantially completed. After the combustion of the sample material was completed, the product was annealed in air at about 420° C. for an additional about 20 min. The body color of the powder appeared orange-yellow and boron-doped WO$_3$ was confirmed by comparison with powder XRD pattern from a standard epsilon WO$_3$ x-ray diffraction (ICFF PDF card number 01-087-2404).

Platinum-Loading of Boron-Doped ε-WO$_3$ 1 g of the product made in the manner described above, and 17.12 mg of [Pt(NH$_3$)$_4$](NO$_3$)$_2$ were placed in 10 mL distilled water and stirred, at about 90° C. for about 2 h in a 40 mL closed vial reactor. The closed vial was then quenched in room temperature tap water and filtered through a membrane filter (0.05 μm pore size), washed with DI water at least 3 times and dried at about 110° C. for overnight (about 15 h), resulting in about 45 mg of 1 wt % platinum-loaded ε-phase WO$_3$.

Sensor Fabrication & Drop Coating of Sensor Material:

About 9 mg of platinum-loaded ε-phase tungsten oxide (1% Pt-ε-WO$_3$) as prepared above, was mixed with isopropyl alcohol (IPA) (0.4 mL) and sonicated for 60 min. About 10×10 μL aliquots of the dispersion were dropped onto a four pin sensor element (0.25×0.25 in electrode, Al$_2$O$_3$ substrate, gold electrode material, P/N 611; Synkera Technologies, Longmont, Colo.), having a surface temperature of about 120° C. and dried between each additional drop. The drop-coated sensor was then baked on under a full-spectrum xenon lamp at 300 W output power, for about 60 min at about 120° C.

Test Chamber with Sensor

TC1 was built in a stainless steel SWAGLOK® jacket, oriented vertically, with the circular ends being the top and bottom of the chamber, and the airflow direction perpendicular to the test chamber's cross section, as shown in FIG. 3. TC1 included an acetone sensor, as described above, mounted on a 4-pin TO-39 header from Synkera Technologies (Longmont, Colo.). The gas sample retention chamber had a volume of about 4.5 mL, about a diameter of 1.2 cm, and a height of about 4 cm. Airflow in the prototype was introduced at the top of the test chamber and flowed down to the sensor at the bottom end of the chamber, where gas flowed out of the chamber.

Figure 5:
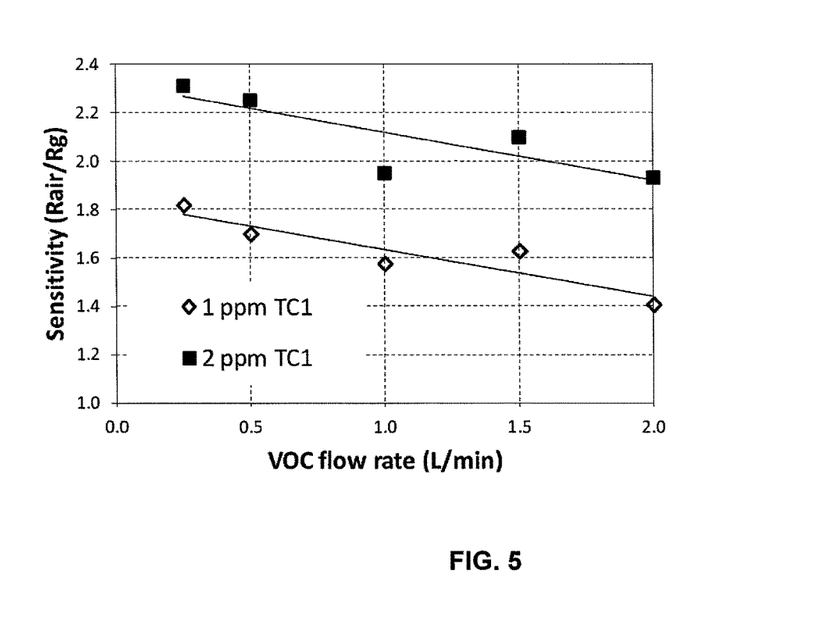
FIG. 5 is a graph depicting the resistivity response to 1 ppm and 2 ppm acetone sample of with the test chamber TC1 as described in Example 1.

To test the sensitivity of the sensor at different flow rates, a mass flow controller (COLE-PARMER® Gas Mass Flow Controller, 5.00-500 mL/min, WO-32907-63, Vernon Hills, Ill.) was used to introduce gas samples into the apparatus in different concentrations of acetone at different flow rates. The mass flow controller was set to 10 s pulse mode to imitate a human breath sample. The sensitivity of the sensor was tested using 1 ppm acetone concentration and 2 ppm acetone concentration and comparing the electrical resistance of the sensor in air to the electrical resistance of the sensor in the test sample. The airflow rate used to test the sensitivity began at about 0.2 L/min and increased to 2 L/min. As the airflow rate increased, the sensor's sensitivity decreased linearly. Results are shown in FIG. 5 and are described in Table 1 below.

TABLE 1

|  | Flow rate (L/min) | Sensitivity (Rair/Rg) | Heater current (Ma) |
|---|---|---|---|
| TC1 1 ppm | 0.25 | 1.82 | 167 |
|  | 0.5 | 1.7 | 172 |
|  | 1 | 1.58 | 178 |
|  | 1.5 | 1.63 | 184 |
|  | 2 | 1.41 | 188 |
| TC1 2 ppm | 0.25 | 2.31 | 167 |
|  | 0.5 | 2.25 | 172 |
|  | 1 | 1.95 | 178 |
|  | 1.5 | 2.1 | 183 |
|  | 2 | 1.93 | 188 |

Example 2

Figure 4:
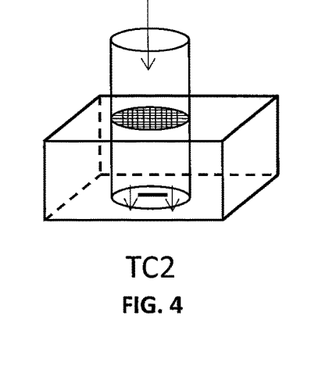
FIG. 4 a schematic of the test chamber TC2 as described in Example 2.
Figure 6:
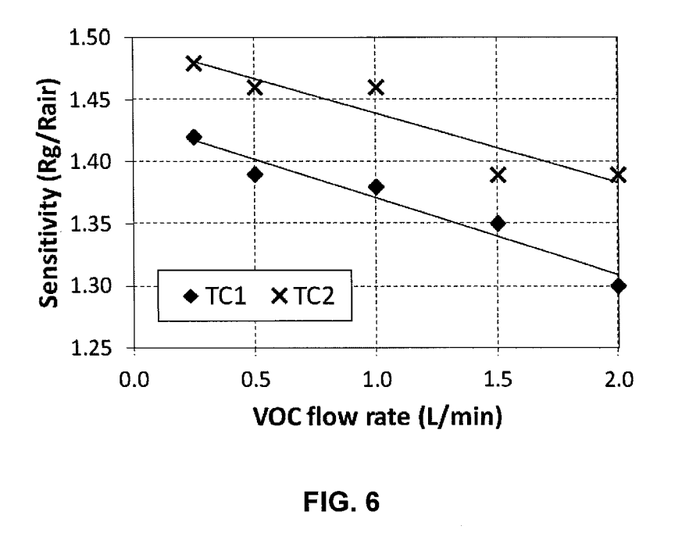
FIG. 6 is a graph depicting the comparative resistivity response to 1 ppm acetone sample with the TC1 and TC2 test chambers.

Test chamber 2 (TC2) was built as in Example 1, but with the addition of an airflow reducing element, as shown as a schematic in FIG. 4. The airflow disrupting element was attached to the inside of the chamber to show the effect of airflow disruption. The airflow disrupting element was a super-corrosion-resistant Type 316 stainless steel wire cloth disc (MCMASTER-CARR® 2930T63, Atlanta, Ga.), with a wire diameter of 0.0045 in, a mesh size of 100×100, an opening size of 0.0055 in, creating an open area of about 30%. The mesh covered about 100% of the cross-section area. Comparative results between TC1 and TC2, both tested at 1 ppm, are shown in FIG. 6. Results are also described in Table 2 below. As shown by the results, the device with a fully covered airflow disrupting mesh had a generally higher sensitivity, but it shows the same flow rate vs. sensitivity relationship, as indicated by the slope of the curve in FIG. 6.

TABLE 2

|  | Flow rate (L/min) | Sensitivity (Rair/Rg) | Heater current (A) |
|---|---|---|---|
| TC1 1 ppm (no mesh) | 0.25 | 1.42 | 0.166 |
|  | 0.5 | 1.39 | 0.172 |
|  | 1.0 | 1.38 | 0.178 |
|  | 1.5 | 1.35 | 0.183 |
|  | 2.0 | 1.30 | 0.188 |
| TC2 1 ppm (airflow disrupting) | 0.25 | 1.48 | 0.160 |
|  | 0.5 | 1.46 | 0.161 |
|  | 1.0 | 1.46 | 0.169 |
|  | 1.5 | 1.39 | 0.174 |
|  | 2.0 | 1.39 | 0.177 |

Example 3

Figure 7:
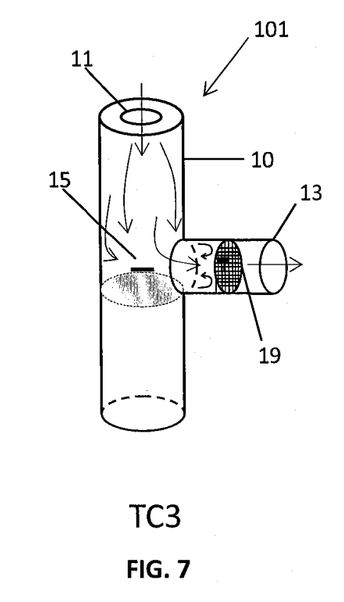
FIG. 7 is a schematic of a test chamber TC3 as described in Example 3.

FIG. 7 shows a schematic of test chamber 3 (TC3). TC3 was built from a 7.62 cm long polycarbonate tube with an inner diameter of 2.6 cm. The TC3 had gas outlet, with a 1 cm inner diameter, forming a perpendicular T-junction with the apparatus chamber, the center of the gas outlet was in line with the sensor. The center of the gas outlet and the sensor (the same sensor as in Example 1) were located 3.81 cm from the end of the apparatus. The apparatus chamber was sealed on the bottom end approximately 4.3 cm from the top, just below the gas outlet aperture. TC3 had a gas inlet that was 1 cm in circumference in the center of the top end of the apparatus. The apparatus also had a wire mesh screen acting as an airflow reducing element filling the gas outlet tube. The airflow reducing element was a super-corrosion-resistant Type 316 stainless steel wire cloth disc, with a wire diameter of 0.01 in, a mesh size of 40×40, an opening size of 0.015 in, creating an open area of about 36% (MCMASTER-CARR® 2930T43, Atlanta, Ga.).

As in Example 1, the sensitivity of the sensor was tested at different airflow rates. The flow rate began at 0.2 L/min and increased to 2 L/min. The sample gas was 1 ppm Acetone and Saturated Moisture gas. The results are described in FIG. 9 and Table 3 below.

TABLE 3

|  | Flow rate (L/min) | Sensitivity (Rair/Rg) | Heater current (A) |
|---|---|---|---|
| TC3 airflow reducing | 0.25 | 1.95 | 0.166 |
|  | 0.5 | 1.71 | 0.172 |
|  | 1.0 | 1.66 | 0.178 |
|  | 1.5 | 1.60 | 0.183 |
|  | 2.0 | 1.44 | 0.188 |
| TC4 airflow disrupting + airflow reducing | 0.25 | 1.80 | 0.164 |
|  | 0.5 | 1.87 | 0.164 |
|  | 1.0 | 1.89 | 0.164 |
|  | 1.5 | 1.84 | 0.167 |
|  | 2.0 | 1.79 | 0.168 |

Example 4

Figure 8:
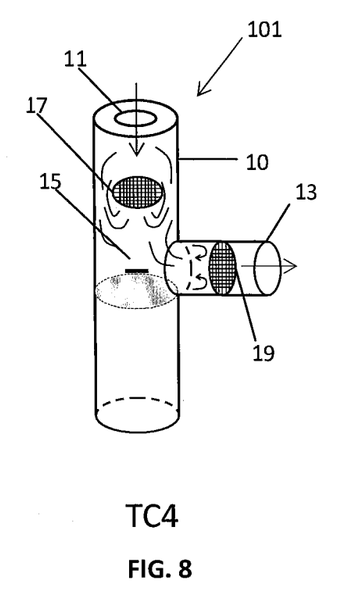
FIG. 8 is a schematic of a test chamber TC4 as described in Example 4.

FIG. 8 shows a schematic of test chamber 4 (TC4). TC4 was built as in Example 2, with the addition of a wire mesh screen that operated as an airflow disrupting element. The airflow disrupting element was suspended in the apparatus by four wire tethers to hold the screen in place. The airflow disrupting element was 1.5 cm in diameter, located in the chamber of the apparatus 1 cm above the surface of the sensor, and concentric with the test chamber tube. The test chamber had an inner diameter of 2.6 cm. The wire mesh screen was a super-corrosion-resistant Type 316 stainless steel wire cloth disc (MCMASTER-CARR® 2930T63, Atlanta, Ga.), with a wire diameter of 0.0045 in, a mesh size of 100×100, an opening size of 0.0055 in, and creating an open area of about 30%. The mesh covered about 70% of the cross-section area. The sensitivity of the apparatus with no mesh airflow reducing element (as in Example 2) compared to the sensitivity as arranged here in Example 3 are displayed in FIG. 9. Also see Table 3 above.

Figure 9:
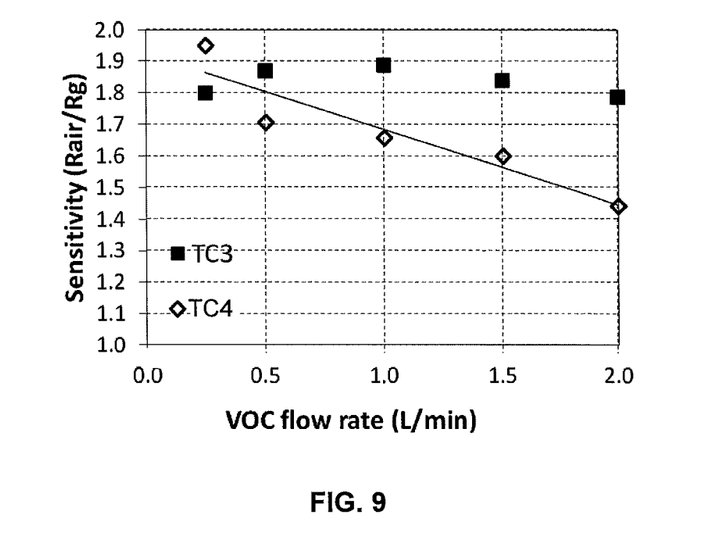
FIG. 9 is a graph depicting the comparative resistivity response to 1 ppm acetone sample of a sensor embodiment TC3 and TC4.

As shown by the results, the device with a partly covered mesh (with annular space between the inner chamber wall and the air flow disrupting element) had less dependence on the flow rate (maintained a more constant sensitivity) than the one without an airflow disrupting element, as indicated by the slope of the curve in FIG. 9 as well as the coefficient of variation in Table 3. In addition, as seen by comparing the results of the device containing both an airflow disrupting element and an airflow reducing element, to the devices containing only an airflow disrupting element or an airflow reducing element (i.e., Example 2 and Example 4), fully covering the sensor with a mesh can improve the sensitivity over the flow rate range, without changing the flow rate vs. sensitivity dependence. However, a sensor that is partly covered with mesh reduces the flow rate vs. sensitivity dependence.

Provisional Patent Application No. 62/064,680, filed Oct. 16, 2014 is incorporated by reference herein in its entirety.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A breath testing apparatus comprising: a chamber configured to retain a gas sample, a gas inlet in fluid communication with the chamber, and a gas outlet in fluid communication with the chamber; a sensor disposed within the chamber, and in fluid communication with the gas inlet and the gas outlet; and an airflow disrupting element disposed within the chamber and sufficiently close to the sensor to change the velocity of air flowing over a surface of the sensor, wherein the airflow disrupting element occupies 95% or less of the cross-sectional area of the chamber and is in fluid communication with the gas inlet, the gas outlet, and the sensor, wherein the sensor comprises boron-doped tungsten oxide.

2. The apparatus of claim 1, wherein the boron-doped tungsten oxide comprises ε-phase $WO_3$.

3. The apparatus of claim 1, wherein the boron-doped tungsten oxide is loaded with platinum.

4. The apparatus of claim 1, wherein the sensor is sensitive to the presence of a volatile organic compound.

5. The apparatus of claim 4, wherein the volatile organic compound is acetone.

6. The apparatus of claim 1, further comprising an electrode in electrical communication with the sensor, and the apparatus is configured to detect a volatile organic compound by a change in resistance of the sensor.

7. An apparatus of claim 1, wherein the airflow disrupting element comprises a mesh screen.

8. The apparatus of claim 7, wherein the open area of the mesh screen is between 5% and 95%.

9. The apparatus of claim 1, wherein the further comprising an airflow reducing element coupled to the gas outlet.

10. The apparatus of claim 9, wherein the airflow reducing element comprises a mesh screen.

11. The apparatus of claim 10, wherein the open area of the airflow reducing element mesh screen is between 15% and 50%.

* * * * *